United States Patent

Brau et al.

[11] Patent Number: 5,575,028
[45] Date of Patent: Nov. 19, 1996

[54] TOOTH FAIRY PILLOW

[76] Inventors: Nancy Brau; Robert Brau, both of 10 Chauser Dr., Greenlawn, N.Y. 11740

[21] Appl. No.: 375,999

[22] Filed: Jan. 20, 1995

[51] Int. Cl.[6] .............................. A47C 20/00; A63H 3/02
[52] U.S. Cl. .................... 5/639; 5/645; 446/296
[58] Field of Search ................ 5/462, 635, 636, 5/639, 907, 645; 446/76, 296, 369, 372

[56] References Cited

U.S. PATENT DOCUMENTS

| | | | |
|---|---|---|---|
| D. 254,891 | 5/1980 | Mills | 5/636 |
| D. 307,846 | 5/1990 | Saeger. | |
| D. 313,141 | 12/1990 | Witter et al.. | |
| D. 329,777 | 9/1992 | Picco. | |
| 4,091,481 | 5/1978 | Redman | 5/639 |
| 4,688,286 | 8/1987 | Miker, Jr. | 5/639 |
| 4,783,866 | 11/1988 | Simmons et al. | 5/441 |
| 5,015,209 | 5/1991 | Ortiz. | |
| 5,016,303 | 5/1991 | Tanaka et al. | 5/437 |
| 5,026,315 | 6/1991 | Chap | 446/372 |
| 5,210,881 | 5/1993 | Stocker, Jr. et al. | 2/247 |

*Primary Examiner*—Steven N. Meyers
*Assistant Examiner*—Robert G. Santos
*Attorney, Agent, or Firm*—Michael I. Kroll

[57] ABSTRACT

A tooth fairy pillow comprising a molar shaped cushion. A large rear pocket is on the molar shaped cushion for holding a toothbrush and a tube of toothpaste which can be used by a child. A small rear pocket is on the large rear pocket for retaining a tooth lost by the child.

5 Claims, 2 Drawing Sheets

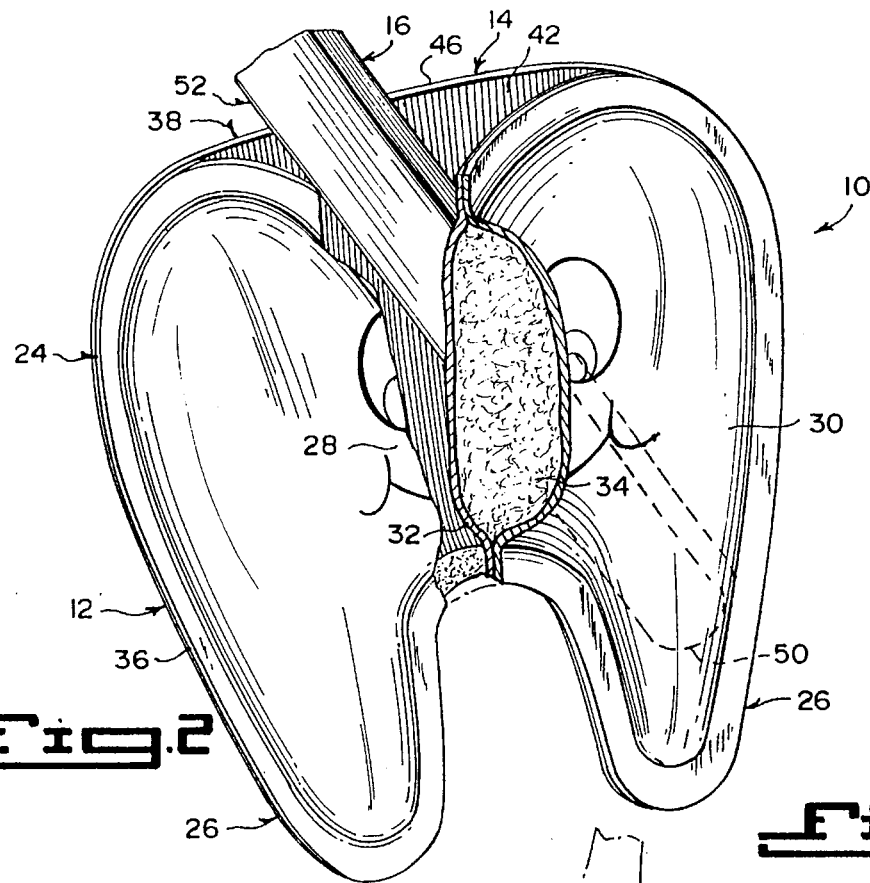
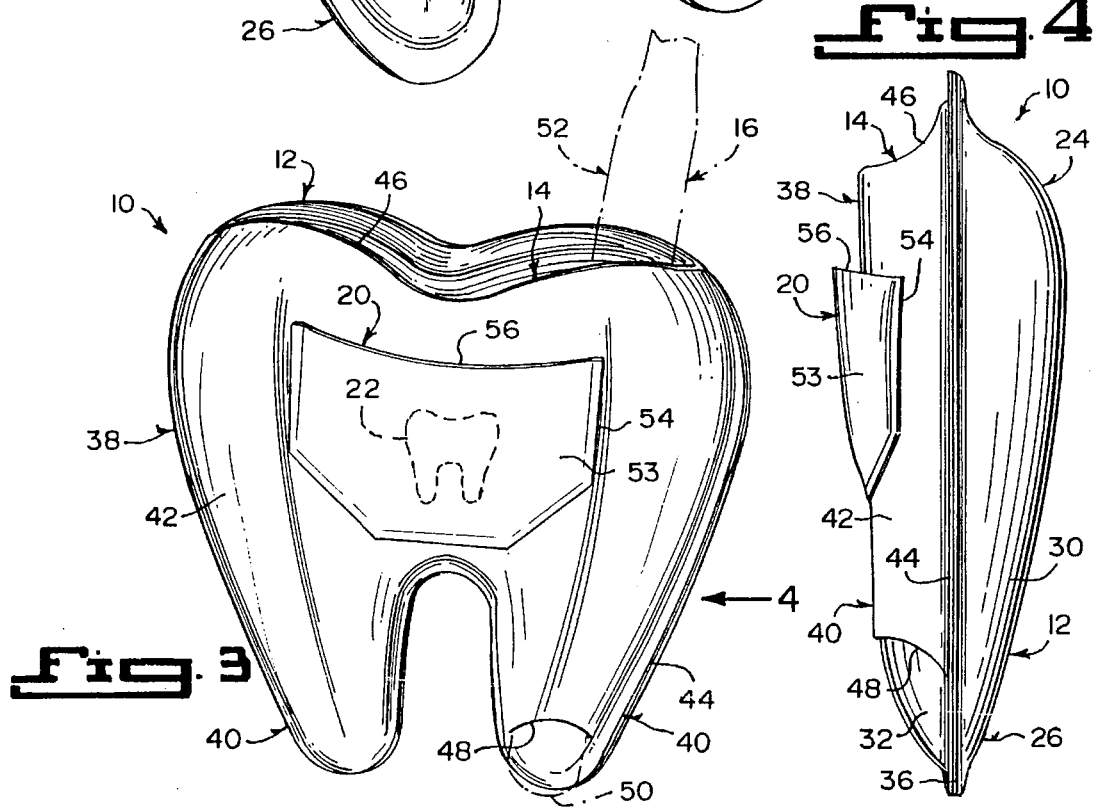

TOOTH FAIRY PILLOW

BACKGROUND OF THE INVENTION

1. Field of the Invention

The instant invention relates generally to tooth shaped articles and more specifically it relates to a tooth fairy pillow.

2. Description of the Prior Art

Numerous tooth shaped articles have been provided in prior art. For example, U.S. Pat. No. Des. 307,846 to Saeger; Des. 313,141 to Witter, deceased et al.; Des. 329,777 to Picco and 5,015,209 to Oritz all are illustrative of such prior art. While these units may be suitable for the particular purpose to which they address, they would not be as suitable for the purposes of the present invention as heretofore described.

SAEGER, KATHRYN L.

TOOTH PILLOW

U.S. Pat. No. Des. 307,846

The ornamental design for a tooth pillow, as shown and described.

FIG. 2 is a rear elevational view thereof;

FIG. 3 is a left side elevational view thereof;

FIG. 4 is a right side elevational view thereof;

FIG. 5 is a top plan view thereof; and

FIG. 6 is a bottom plan view thereof.

Figure 1:
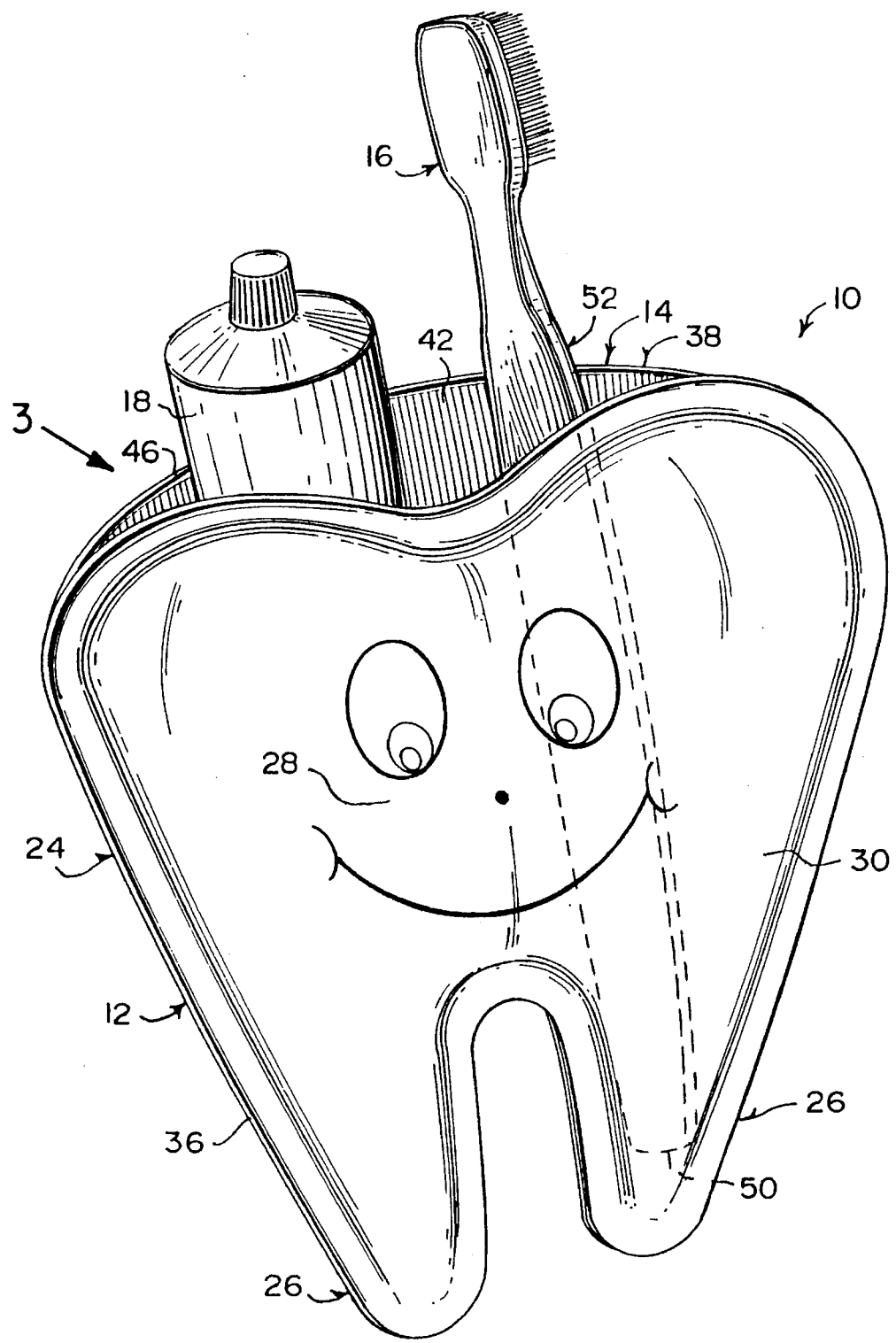
FIG. 1 is a front elevational view of a tooth pillow showing a new design.

WITTER, LINDA L. M. Deceased MADAFFER, LEONA L.

CHILD'S TOOTH PILLOW

U.S. Pat. No. Des. 313,141

The ornamental design for a child's tooth pillow, as shown and described.

FIG. 1 is a front elevation view of a child's tooth pillow showing a new design;

FIG. 2 is a rear elevational view thereof;

FIG. 3 is a top plan view thereof;

FIG. 4 is a bottom plan view thereof; and

FIG. 5 is a right side elevational view thereof, the left side being a mirror image of that shown.

The broken-line showing of the name indicia is for illustrative purposes only and forms no part of the claimed design.

PICCO, BERNADETTE M.

PILLOW

U.S. Pat. No. Des. 329,777

The ornamental design for a pillow, as shown in described.

FIG. 1 is a front elevational view of a pillow showing a new design;

FIG. 2 is a left side elevational view thereof;

FIG. 3 is a right side elevational view thereof;

FIG. 4 is a top plan view thereof;

FIG. 5 is a bottom plan view thereof; and

FIG. 6 is a rear elevational view thereof.

ORTIZ, THERESA

TOOTH FAIRY DOLL

U.S. Pat. No. 5,015,209

The invention relates to a child-playing toy called the "Tooth Fairy Doll", since its basic structure is molar-shaped with two butterfly-like wings at the side. The top of the molar shape is the head and face of the doll, while the two roots of the tooth shape are its legs. To complete the 'tooth fairy' idea, the doll carries two arms with a wand in one. Behind the wings, there is a sack or pouch for the tooth the child has just lost. Overnight, the "Tooth Fairy" takes the tooth out of the sack or pouch and in its place leaves a gift for the child. Fairy-like apparel completes the fantasy.

SUMMARY OF THE INVENTION

A primary object of the present invention is to provide a tooth fairy pillow that will overcome the shortcomings of the prior art devices.

Another object is to provide a tooth fairy pillow that is a molar shaped cushion with a happy face thereon, which contains a large rear pocket for holding a toothbrush and a tube of toothpaste, which can be used by a child.

An additional object is to provide a tooth fairy pillow that contains a small rear pocket on the large rear pocket, which can retain a tooth lost by the child.

A further object is to provide a tooth fairy pillow that is simple and easy to use.

A still further object is to provide a tooth fairy pillow that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views, and wherein:

FIG. 1 is a front perspective view of the instant invention showing a toothbrush and a tube of toothpaste held within a large rear pocket.

FIG. 2 is a front perspective view similar to FIG. 1 with parts broken away, showing the internal structure of the molar shaped cushion.

FIG. 3 is a rear elevational view taken in the direction of arrow 3 in FIG. 1, showing in dotted a tooth held within a small rear pocket.

FIG. 4 is a side elevational view taken in the direction of arrow 4 in FIG. 3.

Similar reference characters denote corresponding features consistently throughout the attached drawings.

DETAILED DESCRIPTION OF THE PREFERRED EMBODIMENTS

Turning now descriptively to the drawings, in which similar reference characters denote similar elements throughout the several views, FIGS. 1 through 4 illustrate a tooth fairy pillow 10, comprising a molar shaped cushion 12. A large rear pocket 14 is on the molar shaped cushion 12, for holding a toothbrush 16 and a tube of toothpaste 18, which can be used by a child. A small rear pocket 20 is on the large rear pocket 14, for retaining a tooth 22 lost by the child.

The molar shaped cushion 12 includes a broad crown portion 24. A pair of tooth root portions 26 are integral with and extends downwardly from the broad crown portion 24. A happy face 28 is imprinted upon the broad crown portion 24.

The molar shaped cushion 12 consists of a front flexible sheet 30, in which the happy face 28 is imprinted upon. A rear flexible sheet 32 is provided. A soft filling 34 is between the front flexible sheet 30 and the rear flexible sheet 32. A sealed edge 36 is about the periphery of the front flexible sheet 30 and the rear flexible sheet 32, to maintain the soft filling 34 therebetween.

The large rear pocket 14 is molar shaped and includes a broad crown segment 38. A pair of tooth root segments 40 are integral with and extend downwardly from the broad crown segment 38. The large rear pocket 14 is a flexible sheet 42 being of the same size and shape as the rear flexible sheet 32 of the molar shaped cushion 12.

The large rear pocket 14 further includes a sealed edge 44 to the rear flexible sheet 32, except along a top edge 46. The large rear pocket 14 can be accessed through the top edge 46. One tooth root segment 40 has a bottom opening 48. A bottom end 50 of a handle 52 of the toothbrush 16 can extend therethrough when the toothbrush 16 is placed within the large rear pocket 14.

The small rear pocket 20 is a flexible sheet 53 being of a smaller size and different shape as the flexible sheet 42 of the large rear pocket 14. The small rear pocket 20 includes a sealed sides and a bottom edges 54 to the large rear pocket 14. The small rear pocket 20 can be accessed through a top edge 56.

The front flexible sheet 30 and the rear flexible sheet 32 of the molar shaped cushion 12 are both fabricated out of a cloth material 58. The flexible sheet 42 of the large rear pocket 14 is fabricated out of the cloth material 58. The flexible sheet 53 of the small rear pocket 20 is fabricated out of the cloth material 58. The cloth material 58 is felt 60. Other types of materials can be used, such as a woven fabric and thin plastic.

OPERATION OF THE INVENTION

To use the tooth fairy pillow, the following steps should be taken:

1. Place the tube of toothpaste 18 and the toothbrush 16 into the large rear pocket 14, so that the child will always have them at hand to brush and clean the teeth.
2. Make sure that the bottom end 50 of the handle 52 of the toothbrush 16 extends through the bottom opening 48 in the tooth root segment 40 of the large rear pocket 14 to be stabilized therein.
3. Place a lost tooth 22 of the child into the small rear pocket 20.
4. Remove the lost tooth 22 overnight from the small rear pocket 20, when the child is asleep.
5. Replace the lost tooth 22 with a gift within the small rear pocket 20, so that the child when waking up will think the tooth fairy was there.

LIST OF REFERENCE NUMBERS 10 tooth fairy pillow
12 molar shaped cushion
14 large rear pocket on 12
16 toothbrush in 14
18 tube of toothpaste in 14
20 small rear pocket on 14
22 tooth in 20
24 broad crown portion of 12
26 tooth root portion of 12
28 happy face on 24
30 front flexible sheet of 12
32 rear flexible sheet of 12
34 soft filling between 30 and 32
36 sealed edge on 30 and 32
38 broad crown segment of 14
40 tooth root segment of 14
42 flexible sheet of 14
44 sealed edge on 14 and 32
46 top edge of 14
48 bottom opening in 40
50 bottom end of 52
52 handle of 16
53 flexible sheet of 20
54 sealed side and bottom edges of 20
56 top edge of 20
58 cloth material for 30, 32, 42 and 53
60 felt of 58

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A tooth fairy pillow comprising:
    a) a molar shaped cushion having a broad crown portion and a pair of tooth root portions integral with and extending downwardly from said broad crown portion and further includes a front flexible sheet on which a happy face is imprinted thereon, a rear flexible sheet, a soft filling between said front flexible sheet and said rear flexible sheet, and a sealed edge about the periphery of said front flexible sheet and said near flexible sheet, to maintain said soft filling therebetween;

b) a large rear pocket on said molar shaped cushion for holding a toothbrush and a tube of toothpaste which can be used by a child, said large rear pocket being molar shaped and includes a broad crown segment and a pair of tooth root segments integral with and extending downwardly from said broad crown segment, said large rear pocket being formed by a flexible sheet being of the same size and shape as said rear flexible sheet of said molar shaped cushion and having a sealed edge to said rear flexible sheet except along a top edge forming a top opening, so that said large rear pocket can be accessed through said top opening, one of said tooth root segments having a bottom opening aligned with said top opening to permit a tooth brush within said large rear pocket to extend out both of the top and bottom openings; and c) a small rear pocket mounted on said large rear pocket for retaining a tooth lost by the child, said small rear pocket being a flexible sheet of a smaller size and different shape than said flexible sheet of said large rear pocket and includes sealed side edges and a sealed bottom edge to said large rear pocket, so that said small rear pocket can be accessed through the top edge.

2. A tooth fairy pillow as recited in claim 1, wherein said front flexible sheet and said rear flexible sheet of said molar shaped cushion are both fabricated out of a cloth material.

3. A tooth fairy pillow as recited in claim 2, wherein said flexible sheet of said large rear pocket is fabricated out of a cloth material.

4. A tooth fairy pillow as recited in claim 3, wherein said flexible sheet of said small rear pocket is fabricated out of a cloth material.

5. A tooth fairy pillow as recited in claim 4, wherein said cloth material is felt.

* * * * *